United States Patent
Kamen et al.

(10) Patent No.: US 9,521,994 B2
(45) Date of Patent: Dec. 20, 2016

(54) SYSTEM AND METHOD FOR IMAGE GUIDED PROSTATE CANCER NEEDLE BIOPSY

(75) Inventors: Ali Kamen, Princeton, NJ (US); Wolfgang Wein, Munich (DE); Parmeshwar Khurd, Princeton, NJ (US); Mamadou Diallo, Plainsboro, NJ (US); Ralf Nanke, Neunkirchen am Brand (DE); Jens Fehre, Hausen (DE); Berthold Kiefer, Erlangen (DE); Martin Requardt, Nürnberg (DE); Clifford Weiss, Baltimore, MD (US)

(73) Assignee: Siemens Healthcare GmbH, Erlangen (DE)

(*) Notice: Subject to any disclaimer, the term of this patent is extended or adjusted under 35 U.S.C. 154(b) by 564 days.

(21) Appl. No.: 12/774,798

(22) Filed: May 6, 2010

(65) Prior Publication Data
US 2010/0286517 A1 Nov. 11, 2010

Related U.S. Application Data

(60) Provisional application No. 61/176,969, filed on May 11, 2009.

(51) Int. Cl.
*A61B 8/00* (2006.01)
*G06K 9/00* (2006.01)
(Continued)

(52) U.S. Cl.
CPC .......... *A61B 10/0241* (2013.01); *A61B 8/4254* (2013.01); *A61B 34/20* (2016.02);
(Continued)

(58) Field of Classification Search
CPC ................ G06T 7/0012; G06T 7/0083; G06T 2207/20144; G06T 2207/20081
(Continued)

(56) References Cited

U.S. PATENT DOCUMENTS 4,443,855 A * 4/1984 Bishop et al. ................ 700/259
6,037,914 A * 3/2000 Robinson .......................... 345/7
(Continued)

FOREIGN PATENT DOCUMENTS

EP 0915434 A2 5/1999
WO WO03039370 5/2003
(Continued)

OTHER PUBLICATIONS

"Foskey et al.," "Large deformation three-dimensional image registration in image-guided radiation therapy," Physics in Medicine and Biology, 50: 5869-5892, 2005.*
(Continued)

*Primary Examiner* — Tse Chen

(57) ABSTRACT

In a method for image guided prostate cancer needle biopsy, a first registration is performed to match a first image of a prostate to a second image of the prostate. Third images of the prostate are acquired and compounded into a three-dimensional (3D) image. The prostate in the compounded 3D image is segmented to show its border. A second registration and then a third registration different from the second registration is performed on distance maps generated from the prostate borders of the first image and the compounded 3D image, wherein the first and second registrations are based on a biomechanical property of the prostate. A region of interest in the first image is mapped to the compounded 3D image or a fourth image of the prostate acquired with the second modality.

16 Claims, 7 Drawing Sheets

(51) Int. Cl.
*A61B 10/02* (2006.01)
*A61B 17/00* (2006.01)
*A61B 17/34* (2006.01)
*A61B 18/00* (2006.01)

(52) U.S. Cl.
CPC ............ *A61B 2017/00274* (2013.01); *A61B 2017/00694* (2013.01); *A61B 2017/3413* (2013.01); *A61B 2018/00547* (2013.01); *A61B 2034/105* (2016.02); *A61B 2034/107* (2016.02); *A61B 2034/2051* (2016.02); *A61B 2090/367* (2016.02); *A61B 2090/374* (2016.02); *A61B 2090/378* (2016.02)

(58) Field of Classification Search
USPC ....................................................... 600/438
See application file for complete search history.

(56) References Cited

U.S. PATENT DOCUMENTS

| | | | |
|---|---|---|---|
| 6,137,898 A * | 10/2000 | Broussard | B29C 49/0021 382/132 |
| 6,283,917 B1 * | 9/2001 | Jago et al. | 600/437 |
| 6,466,815 B1 | 10/2002 | Saito | |
| 6,731,800 B1 * | 5/2004 | Barthel et al. | 382/176 |
| 7,280,710 B1 * | 10/2007 | Castro-Pareja et al. | 382/303 |
| 8,700,126 B2 * | 4/2014 | Li | 600/407 |
| 2005/0187473 A1 * | 8/2005 | Boctor et al. | 600/437 |
| 2007/0036402 A1 * | 2/2007 | Cahill et al. | 382/128 |
| 2008/0161687 A1 | 7/2008 | Guo | |
| 2008/0221425 A1 | 9/2008 | Olsen et al. | |
| 2008/0247622 A1 * | 10/2008 | Aylward | A61B 19/52 382/131 |
| 2009/0028397 A1 * | 1/2009 | Makram-Ebeid | 382/128 |
| 2009/0046912 A1 * | 2/2009 | Hostettler et al. | 382/131 |
| 2009/0316966 A1 * | 12/2009 | Marshall | A61B 6/5217 382/128 |
| 2009/0326363 A1 | 12/2009 | Li et al. | |

FOREIGN PATENT DOCUMENTS

| | | |
|---|---|---|
| WO | 2006089426 A1 | 8/2006 |
| WO | WO 2006/089426 * | 8/2006 |
| WO | WO2006/089426 A1 | 8/2006 |
| WO | WO 2008/065600 * | 6/2008 |
| WO | 2009052497 A2 | 4/2009 |

OTHER PUBLICATIONS

"Rohde et al.," "A Comprehensive Approach for Multi-channel Image Registration," published Mar. 2007 at http://www.contrib.andrew.cmu.edu/~gustavor/rohde_wbir03.pdf, pp. 1-10.*

Perrotti M, Han KR, Epstein RE, et al. Prospective evaluation of endorectal magnetic resonance imaging to detect tu mor foci in men with prior negative prostatic biopsy: a pilot study. J. Urol 1999; 162:1314-1317. [CrossRef][Medline].

Wein W. Brunke S, Khamene A, Callstrom MR, Navab N. Automatic CT-Ultrasound Registration for Diagnostic Imaging and Image-guided Intervention. Medical Image Analysis 12(5), pp. 577-585, Oct. 2008.

Japanese Office Action and Translation mailed Dec. 16, 2013 corresponding to Japanese Application No. 2012-510898 filed May 10, 2010 (10 pages).

Chen et al., GPU-based point radiation for interactive volume sculpting and segmentation, The Visual Computer, 24 (7-9): 689,698, (2008).

* cited by examiner

410

SYSTEM AND METHOD FOR IMAGE GUIDED PROSTATE CANCER NEEDLE BIOPSY

CROSS-REFERENCE TO RELATED APPLICATION

This application claims the benefit of U.S. Provisional Application No. 61/176,969, filed May 11, 2009, the disclosure of which is incorporated by reference herein in its entirety.

BACKGROUND OF THE INVENTION

1. Technical Field

The present invention relates to prostate biopsy, and more particularly to, increasing the sensitivity of prostate biopsy procedures for detecting cancer.

2. Discussion of the Related Art

Prostate cancer is currently diagnosed by using transrectal ultrasonography (US)-guided needle biopsy, which is prescribed as a result of an elevated prostate-specific antigen (PSA) level or on account of the detection of a palpable nodule during a digital rectal exam (DRE). The introduction of image-guided biopsy with US substantially increased the accuracy of biopsy, resulting in transrectal US guidance becoming the universally accepted method for prostate biopsy. This increase in accuracy is compared to that of a completely blind biopsy. While transrectal US-guided biopsy is a clinically accepted method, the overall procedure results demonstrate a low sensitivity of around 60%, with only around a 25% positive predictive value. Consequently, repeat biopsies are required. For example, in more than 20% of cancer studies, there is a requirement of more than one biopsy session to reach a diagnosis decision.

Magnetic Resonance (MR) imaging can clearly depict not only the prostate gland but also its substructure including the central, transitional, and peripheral zones. T2-weighted images can demonstrate nodules in the peripheral zone. Localizing the tumor foci and the peripheral zone with MR imaging before the prostate biopsy may increase the overall cancer detection rate. In addition, functional information can be acquired with techniques like diffusion weighted imaging (DWI), dynamic contrast imaging (DCE), and chemical shift imaging (CSI) to further characterize the prostatic tumor tissue. Using this information during US-guided biopsy can improve the sensitivity of the biopsy procedure. For example, in a known technique, endorectal MR imaging findings of suspected tumor foci were used to guide the placement of needles during transrectal US-guided biopsy. By localizing suspected tumor lesions or targets on the endorectal MR image and by visually correlating the locations to US images during transrectal US-guided biopsy, the accuracy of the transrectal US-guided biopsy, aided by using MR imaging, was 67% in a study of 33 patients. The data for this study underwent a tedious visual inspection, which cannot be implemented as a clinical routine.

There exists a need to enhance the sensitivity in detecting malignant lesions during a prostate biopsy procedure.

SUMMARY OF THE INVENTION

In accordance with an exemplary embodiment of the present invention, disclosed are a system and method to use magnetic resonance (MR) imaging for prostate biopsy to localize tumors and their peripheral zone and use this information during an ultrasound (US) exam to place needles into focal lesions. The method focuses on the automation of this process, which is required for clinical implementation. The system facilitates implementation of the image acquisition process. Further, navigation software with specific features is disclosed to handle processing and visualization steps within the overall procedure.

Exemplary embodiments of the present invention provide a method and system for image guided prostate cancer needle biopsy.

The method comprises receiving a first image of a prostate, wherein the first image is acquired with a first imaging modality and is segmented to show a border of the prostate; acquiring a second image of the prostate, wherein the second image is acquired with a second imaging modality; performing a first registration to match an orientation of the first image to an orientation of the second image and a feature of the prostate in the first and second images; acquiring third images of the prostate, wherein the third images are acquired with the second imaging modality and compounded into a three-dimensional (3D) image; segmenting the prostate in the compounded 3D image to show a border of the prostate by using parameters of the first registration and a binary mask of the prostate in the first image; performing a second registration and then a third registration different from the second registration on distance maps generated from the prostate borders, wherein the first and second registrations are based on a biomechanical property of the prostate; and mapping a region of interest in the first image to the compounded 3D image or a fourth image of the prostate acquired with the second modality, wherein the mapping is based on a result of the second and third registrations.

The first imaging modality is magnetic resonance and the second imaging modality is ultrasound (US).

The orientations of the first and second images comprise axial, sagittal or coronal.

The matched feature of the prostate comprises a center of the prostate.

The third images of the prostate are acquired by a US fan sweep.

Segmenting the prostate in the compounded 3D image to show a border of the prostate comprises generating foreground and background seeds from the binary mask, wherein the foreground seeds are generated by shrinking the binary mask in the compounded 3D image and the background seeds are generated by expanding the binary mask in the compounded 3D image.

The second registration is a rigid registration and the third registration is a deformable registration.

The method further comprises displaying the compounded 3D image or the fourth image with the region of interest mapped thereon.

The method further comprises visually tracking a biopsy needle in the compounded 3D image or the fourth image.

The method further comprises storing the location of the region of interest in memory and noting whether the region of interest has been biopsied.

The method further comprises displaying a projected needle path on the compounded 3D image or the fourth image with the region of interest mapped thereon.

The first image includes a plurality of regions of interest, the method further comprises storing locations of the regions of interest.

The method further comprises registering the fourth image to the compounded 3D image and then mapping the region of interest to the fourth image.

The biomechanical property of the prostate comprises the prostate's elasticity.

The system comprises a memory device for storing a program; and a processor in communication with the memory device, the processor operative with the program to: receive a first image of a prostate, wherein the first image is acquired with a first imaging modality and is segmented to show a border of the prostate; receive a second image of the prostate, wherein the second image is acquired with a second imaging modality; receive parameters of a first registration in which an orientation of the first image is matched to an orientation of the second image and a feature of the prostate in the first and second images is matched; receive third images of the prostate, wherein the third images are acquired with the second imaging modality and compounded into a 3D image; segment the prostate in the compounded 3D image to show a border of the prostate, wherein the segmentation uses parameters of the first registration and a binary mask of the prostate in the first image; perform a second registration and then a third registration different from the second registration on distance maps generated from the prostate borders, wherein the first and second registrations are based on a biomechanical property of the prostate; and map a region of interest in the first image to the compounded 3D image or a fourth image of the prostate acquired with the second modality, wherein the mapping is based on a result of the second and third registrations.

The system further comprises a US device that provides the second image, third images or fourth image.

The processor is further operative with the program to: display the compounded 3D image or the fourth image with the region of interest mapped thereon; and display an image of a biopsy needle in the compounded 3D image or the fourth image.

The system further comprises a device that tracks the biopsy needle.

The system further comprises a device that tracks an ultrasound probe.

Another method comprises: acquiring a 3D tracked US sweep of a prostate and generating a compounded 3D US image from the sweep; registering the compounded 3D US image with a MR image of the prostate, wherein the registration comprises performing a rigid registration and then a deformable registration on distance maps generated from segmentations of the prostate in the MR and US images, wherein the rigid and deformable registrations are based on a biomechanical property of the prostate; and transferring a marker identifying a region of interest that is believed to include a lesion from the MR image to the compounded 3D US image or a real-time US image.

DETAILED DESCRIPTION OF EXEMPLARY EMBODIMENTS

Figure 1:
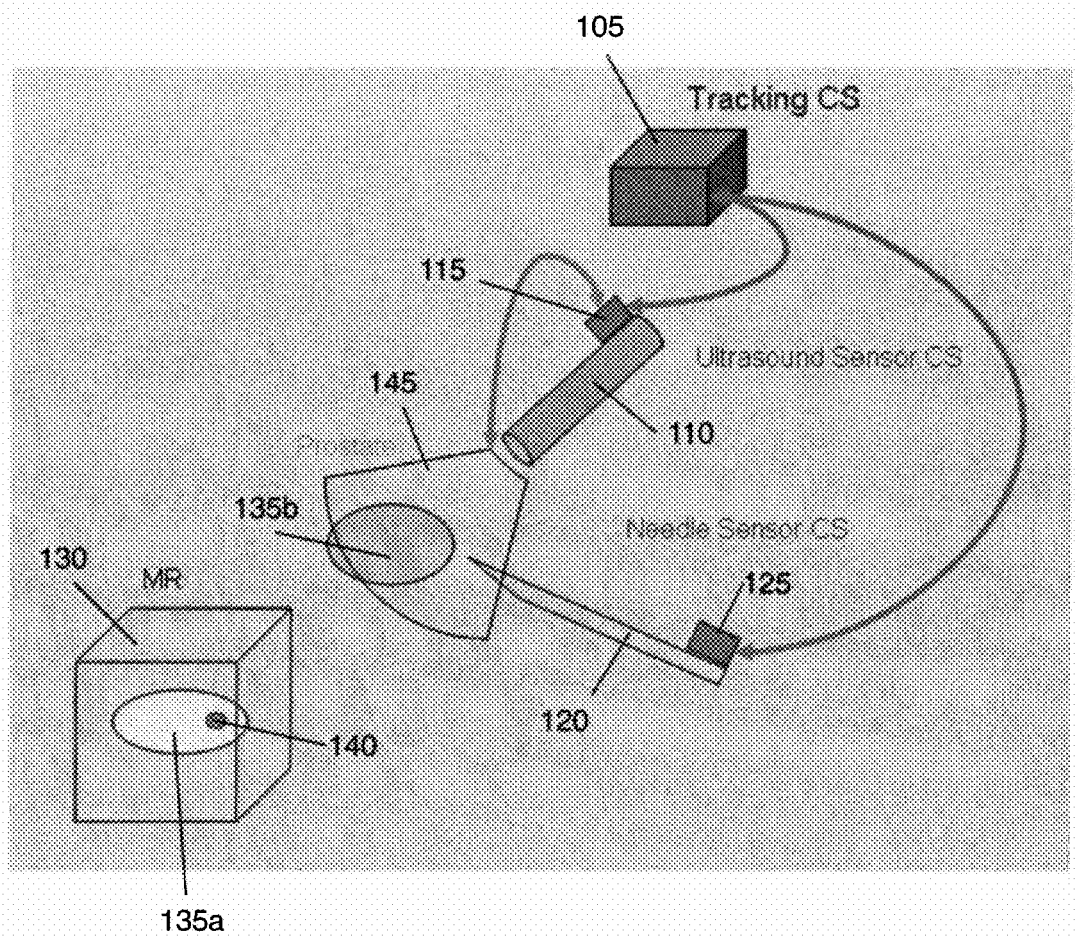
FIG. 1 illustrates, according to an exemplary embodiment of the present invention, a system.

In FIG. 1, there is shown, according to an exemplary embodiment of the present invention, a system. The system includes an external tracking system 105 that tracks an ultrasound (US) probe 110 in a stationary coordinate system, the so-called fixed coordinate system. The probe 110, which may be a transducer, is tracked by placement of a tracking sensor 115 on the probe 110. A needle 120, which used for biopsy purposes, may also be tracked by placement of a tracking sensor 125 on the needle 120. The system further includes a computer (not shown but described later in FIG. 7) that can cause a reference image, for example, a magnetic resonance (MR) image 130 of a prostate 135*a* that includes a lesion 140, to be displayed.

Briefly, the tracking information of the US probe 110 along with calibration information of the US probe 110 enables generation of pseudo three-dimensional (3D) data sets that consist of arbitrarily (due to freehand acquisition) oriented two-dimensional (2D) US images in 3D. On the other hand, reference data (e.g., the MR image 130) is specified in the coordinate system of the scanning device used to acquire the MR image 130. An image based registration technique, according to an exemplary embodiment of the present invention, establishes the transformation that is required to map the reference MR image 130 onto the US images in 3D. The specifics of this registration and the dependent components required for this registration process are discussed throughout the remainder of this disclosure.

Before proceeding, however, some of the challenges associated with image based registration of reference MR images to US will be discussed. For example, the appearance of the prostate in US and MR are completely different. This makes it hard to establish the corresponding structure across these two acquisitions. In addition, US acquisition causes local deformations of the prostate in a different way as compared to the deformation applied as a result of the transrectal coil used during MR and or no deformation in the case where the coil is not used.

These two translate to challenges in first establishing a robust image similarity measure, and second having this similarity measure/metric work in a deformable registration framework.

Figure 2:
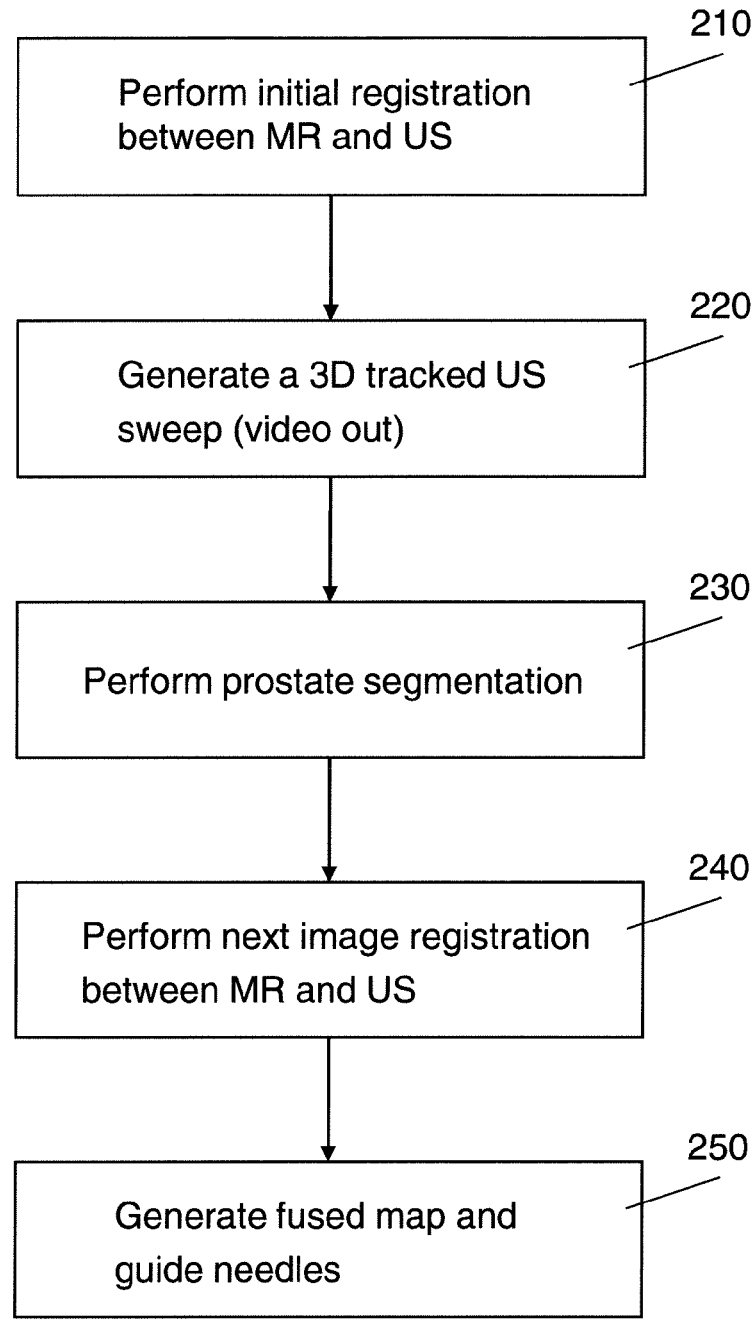
FIG. 2 illustrates, according to an exemplary embodiment of the present invention, a method.

The method, according to an exemplary embodiment of the present invention, overcomes these two challenges. The steps of the method are shown in FIG. 2. For example, in FIG. 2, an initial registration of MR and US images is performed (210). A 3D tracked US sweep (video out) is generated (220). The prostate is segmented in a compounded 3D image of the prostate, the compounded image being generated by the US sweep (230). Image registration is again performed between MR and US images (240). A fused map is generated and needles are guided (250). A detailed description of this process is now provided.

Figure 3:
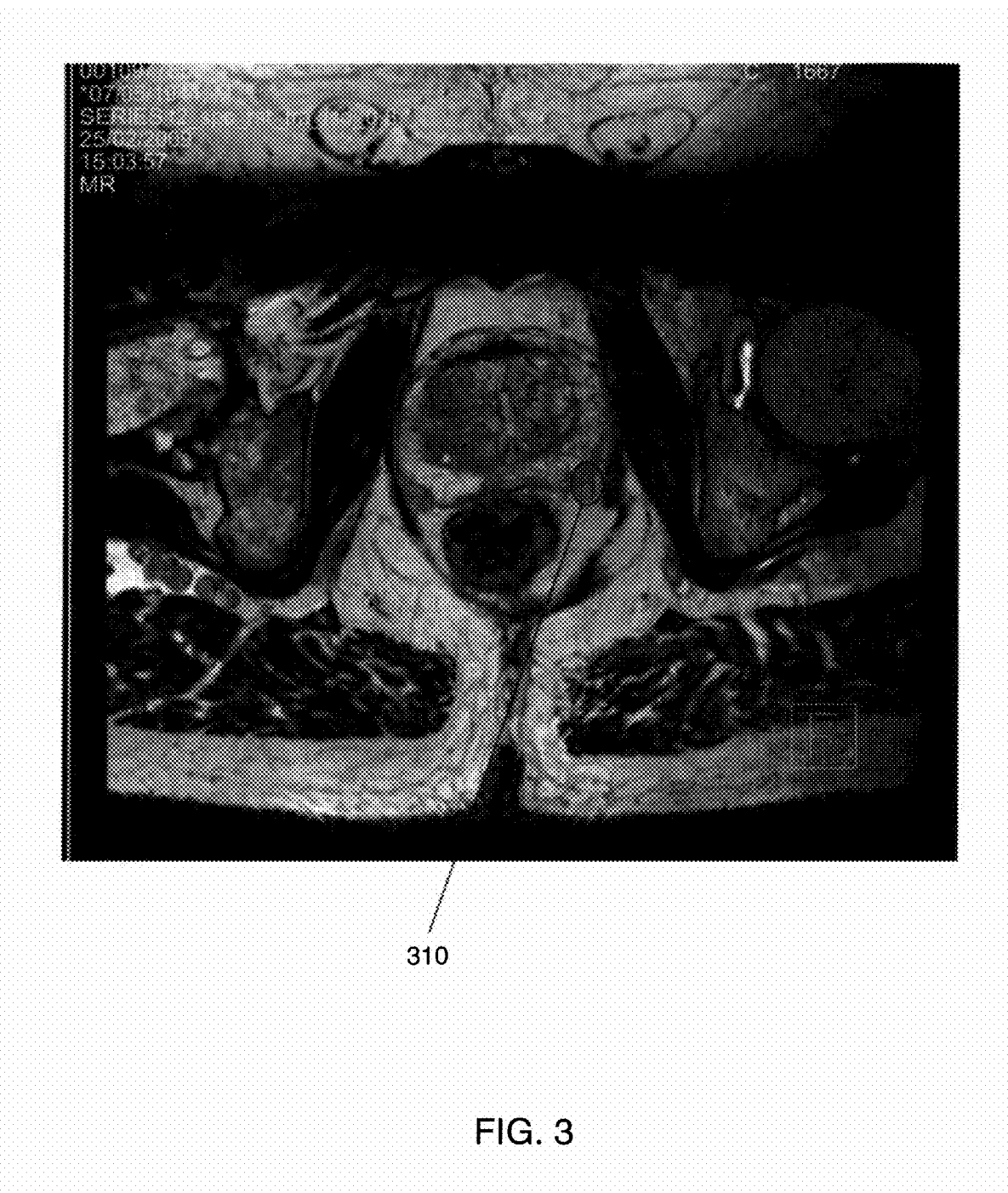
FIG. 3 illustrates, according to an exemplary embodiment of the present invention, a prostate segmented on a planning magnetic resonance (MR) image.

1—During a planning phase (prior to the 3D tracked sweep in FIG. 2), a semi-automatic segmentation on 3D planning data (e.g., MR) is performed. Here, the binary mask or contours of the prostate are saved. FIG. 3 shows the prostate delineated from MR. The prostate's border is identified by reference numeral 310 in FIG. 3. Suspicious regions are also identified in the prostate with multi-parametric MR. This data is used to plan where the biopsy is to take place and the planning information is recorded.

2—During a US-guided biopsy session, a 3D sweep (see reference numeral 145 in FIG. 1 for an example of a sweep) of tracked US images using magnetic tracking system is performed. Here, a 3D US machine may be used. A 2D US machine may be used as well; however, this requires the US probe to have a sensor (see the probe-sensor configuration of FIG. 1, for example).

3—An initial rigid alignment is performed between the MR and US images. This is done to compensate for orientation misalignments between the US image and MR image. This is done by first acquiring a standard view of the prostate (axial, sagittal or coronal) using US and then matching the orientation to that of MR. The standard view is achieved by having a medical professional manipulate the US probe to get the prostate in the center of the US image, for example. This is done free hand.

4—With the MR and US images in matching orientations, manual adjustment of the translation is performed to account for translational misalignments between MR and US images. Here, the medical professional slides an MR image over an US image to match the MR image with the content of US images. For example, the center of the prostate gland is matched in both MR and US images.

5—Tracked 2D US images are compounded into a 3D volume. Here, a 3D US sweep covering the prostate (see prostate 135b in FIG. 1) is acquired. Here, the 3D tracked sweep is built to a bounded Cartesian volume and the sequence of 2D images is re-sampled into a 3D volume.

Figure 4:
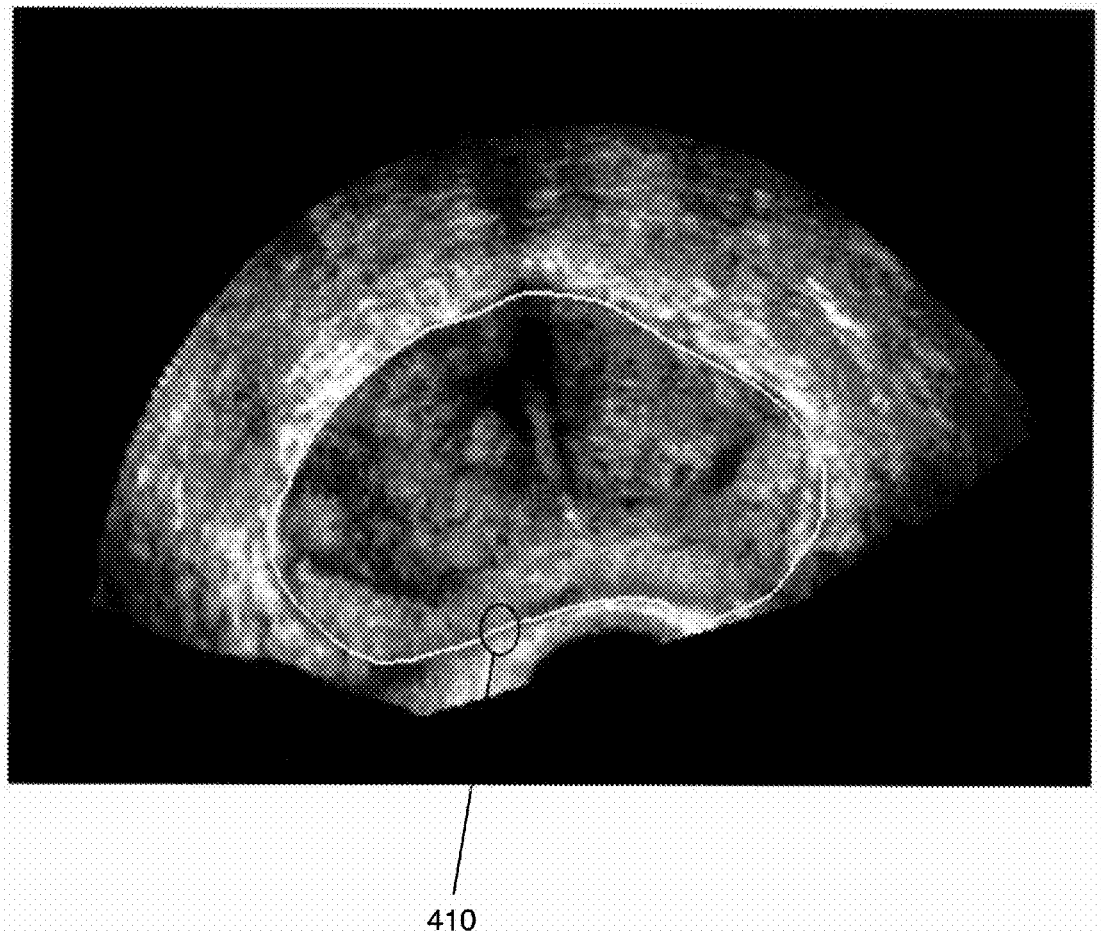
FIG. 4 illustrates, according to an exemplary embodiment of the present invention, a prostate segmented on a compounded ultrasound (US) image.

6—The prostate is segmented in the compounded 3D us image by using the established initial registration between MR and US, and the MR based binary mask from the planning phase. FIG. 4 shows the prostate segmented on the compounded US image. The prostate's border is identified by reference numeral 410 in FIG. 4. The steps of segmenting the prostate in the compounded US image are as follows. Generate foreground and background seeds from the binary mask that allow for variations in shape. The foreground seeds are generated, for example, by shrinking the mask by around 20%. The background seeds are generated, for example, by expanding the mask by around 20%. The percentage of expansion and shrinkage accounts for the variations in shape due to rigid registration and possible deformations that exist across the two acquisitions. Essentially, what occurs here is the prostate boundary in MR is overlaid on the US image and the boundary of the prostate in the US image is determined.

Figure 5:
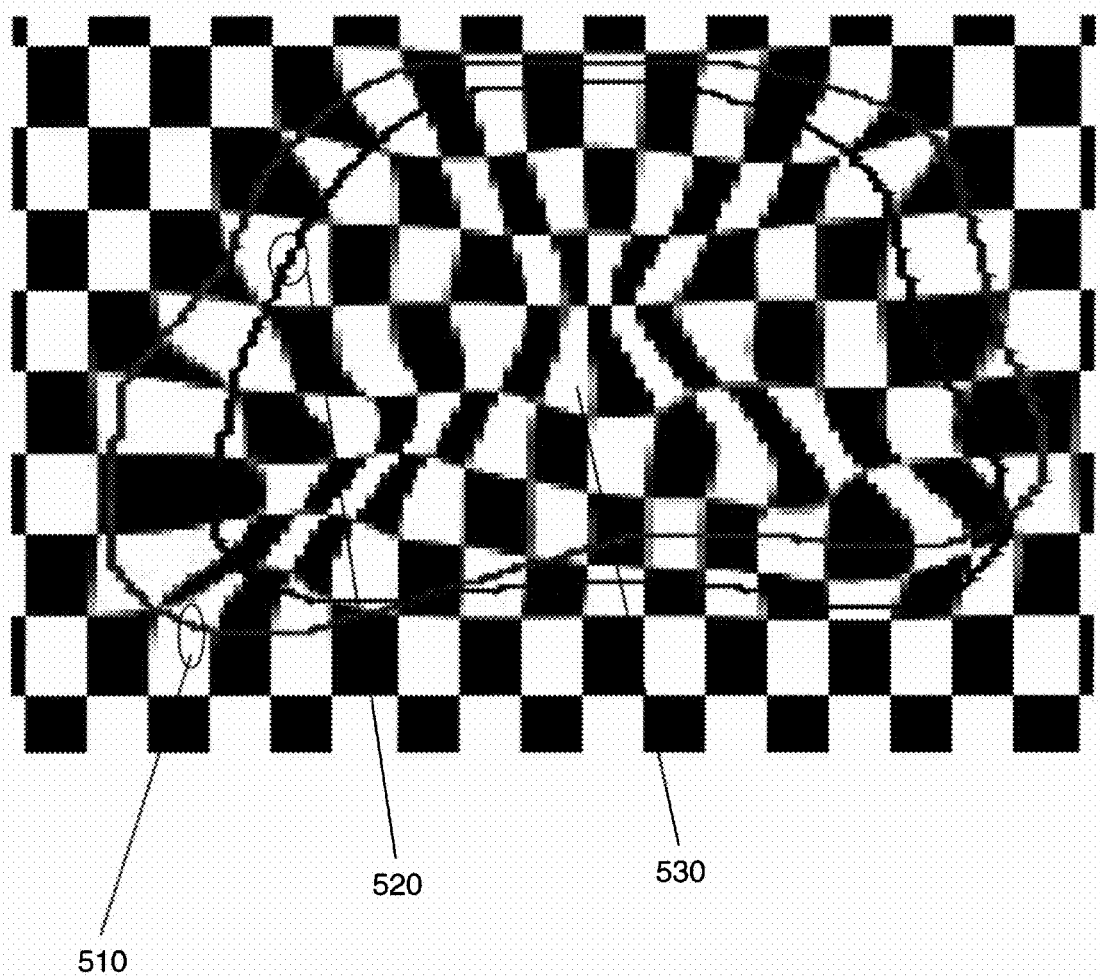
FIG. 5 illustrates, according to an exemplary embodiment of the present invention, prostate registration and an underlying deformation based on the segmentations of FIGS. 3 and 4.

7—The segmentations of the prostate in MR and US are used to first perform rigid and then deformable (adjusted by the elasticity of the prostate) registration. In other words, the mesh surfaces from MR and US are registered considering rigid transformation and elastic deformation (biomechanical properties). The registration is done on the distance maps generated from the boundary of the segmentations. The distance map registration spreads discrepancies between the contours uniformly within the prostate. This is equivalent to extracting the internal object movements as the results of the applied force to the object surface. FIG. 5 shows the registered prostate boundaries (510-MR; 520-US) and the underlying deformation field (warped mesh indicated by reference numeral 530).

8—The planning MR image is transformed along with all the annotations and segmentation structures onto the compounded US image or another live acquired US image. In other words, once the deformation field is found the suspicious regions (e.g., lesions) are transferred (e.g., mapped) from the MR image to the US image.

Figure 6:
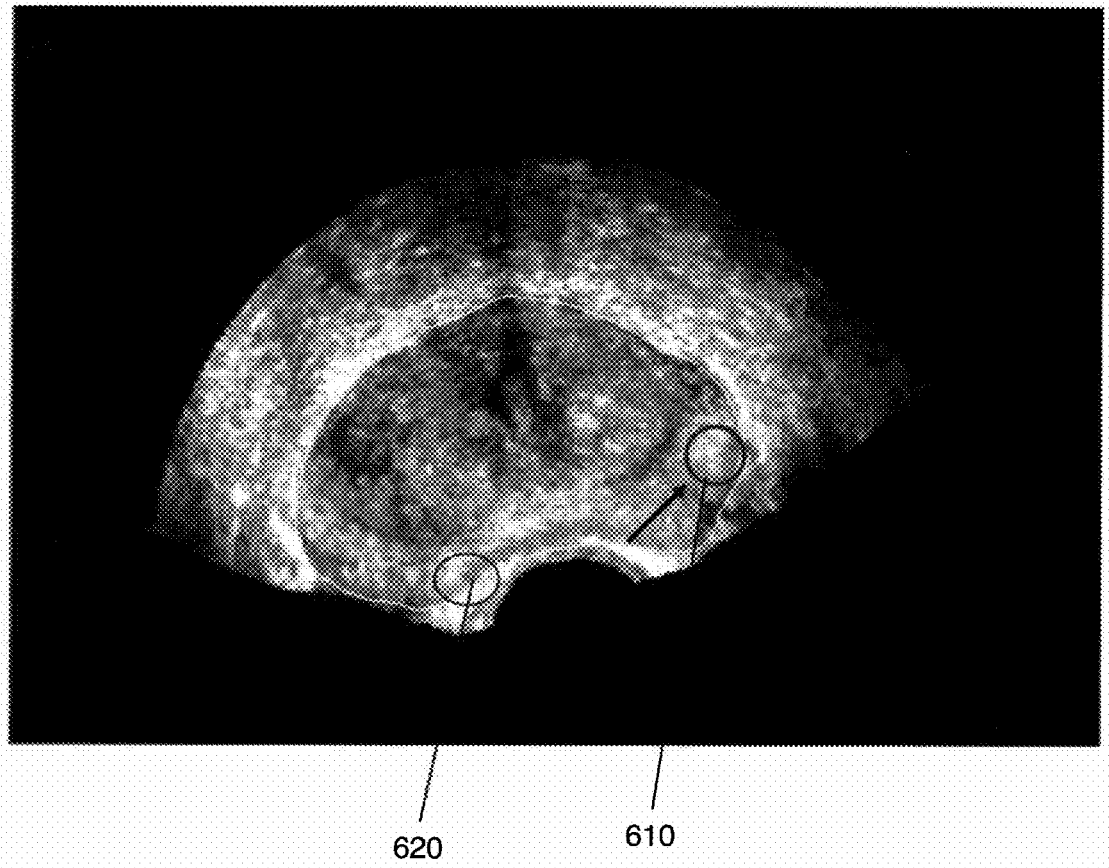
FIG. 6 illustrates, according to an exemplary embodiment of the present invention, ultrasound with a specified target area imported from MR and a projected needle path.

9—The abstract annotations of the points of interest (such as target points for biopsy) transformed from the MR images onto the real-time US (or recorded US) using the established transformation are displayed. FIG. 6 shows a US image with a lesion location 610 (which is a target point for biopsy) mapped from an MR image. FIG. 6 also shows the prostate's border 620. Due to magnetic position tracking, the corresponding MR image and target information can be correctly visualized on US at any time. Appropriate superimposition options (direct MRI overlay, color blending, structure overlay, etc.) allow the user to monitor the quality of alignment, and re-run the registration workflow if it deteriorates due to bad patient immobilization or anatomic shifts (e.g., repeat steps 2, 5-8 and additionally 3-4 for large misalignments).

Disclosed hereinafter are variations and extensions of the present invention.

Mechanical and/or optical as opposed to magnetic position and orientation tracking systems can be used to track the ultrasound probe.

3D wobblers or 2D matrix airways can be used to generate a native 3D US volume as opposed to a compounded 3D volume from a set of tracked 2D US images.

Multislice 2D MR acquisition can be used as opposed to a single 3D-MR planning dataset.

A series of 2D and 3D acquisitions can be used as opposed to a single 2D or 3D planning dataset (e.g., T2 weighted MR acquisitions to acquire morphologic information as well as acquisitions to acquire functional information (e.g., diffusion weighted imaging, dynamic contrast imaging, and chemical shift imaging)). The acquisitions could come from either a single scanning session or various time points. Registration is required to bring the series of acquisitions into a single coordinate frame for the case where various acquisitions are performed.

Use the tracking system and patient global orientation to roughly align the ultrasound images with planning datasets, where the patient's orientation is specified.

Use another set of 3D or 2D US images as opposed to MR for fusion and visualization. These 3D and 2D US images could be processed to extract some additional information (e.g., lesion detection) or just be used as is without added processing.

Use user specified point correspondences (e.g., single point in middle of prostate for example on the urethra in both MR and US images) to compute the rough translations. If three or more point correspondences are specified, a rigid registration estimate and an initial guess for the amount of anatomic deformations can be computed automatically.

A full automatic segmentation method can be used to segment the prostate on the planning data.

A different segmentation method, such as shape model constrained segmentation based on level-sets or machine learning based approaches, can be used to segment the prostate for the US acquisitions.

Biomechanical finite element based registration can be used to register the extracted boundaries of the segmentations of the prostate in MR and US to create physically plausible deformations.

Instead of or after the contour-based registration, execute an automatic algorithm operating directly in the MR and US image intensities similar to that described in Wein et al. "Automatic CT-Ultrasound Registration for Diagnostic Imaging and Image-Guided Intervention." Medical Image Analysis 1295), pp 577-585, October 2008. This can increase the registration accuracy, because the prostate outline itself is poorly visualized with US, while some internal structures might correspond better to their counterparts from MR. In another embodiment, MR image intensities can be mapped onto roughly estimated acoustic impedance values, and then both the original MR image intensities and the impedance values can be used to create a multi-channel simulation of US from MR images. Using an appropriate advanced local similarity metric, it can be compared to the actual 3D US images (taking their 2D/3D imaging geometry into account), and a non-linear optimization refines the deformable transformation parameters with respect to this similarity.

In addition to the visual monitoring of registration alignment (workflow step 9 above), automatic image based validation and/or active refinement of the registration based on the live US image plane can be done.

Instead of, or in addition to standard B-mode US imaging, different imaging modes such as elastography (including acoustic radiation force imaging—ARFI) or contrast imaging protocols, may be used.

Figure 7:
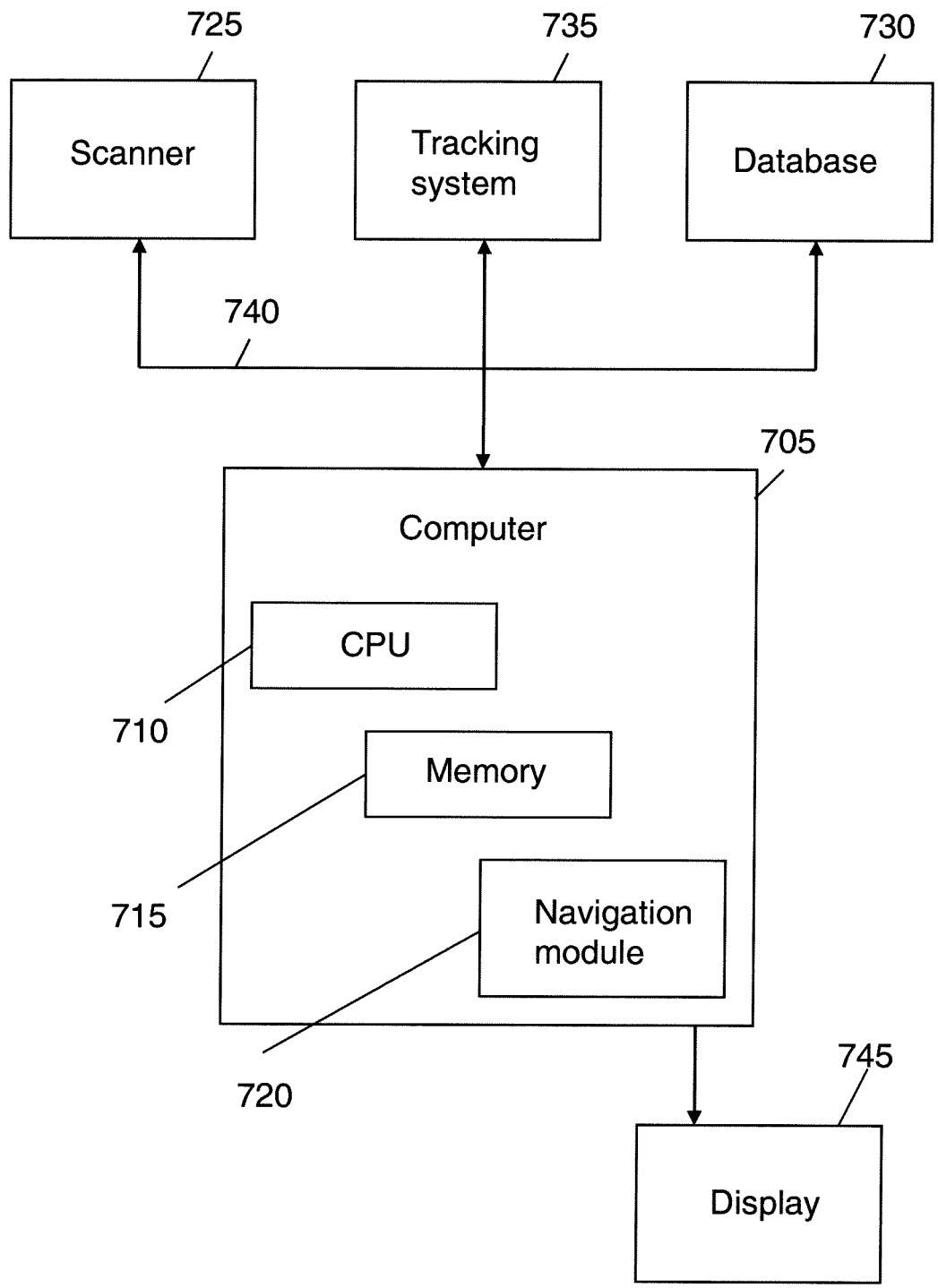
FIG. 7 illustrates, according to an exemplary embodiment of the present invention, a computer.

A computer in which exemplary embodiments of the present invention may be implemented will now be described with reference to FIG. 7. As shown in FIG. 7, the computer 705 has access to a scanner 725, a database 730 and tracking system 735 through a wired or wireless network 740. The scanner 725 may be an MR or other type of scanner that is capable of functional imaging or a US scanner, for example. Image data acquired by the scanner 725 may be provided directly to the database 730 for subsequent access by the computer 705. The tracking system 735 may be optical, magnetic or mechanical. A US probe and/or biopsy needle may be communicatively coupled to the tracking system 735 and computer 705. The computer 705 includes, inter alia, a central processing unit (CPU) 710, a memory 715 and a navigation module 720 that includes program code for executing methods in accordance with exemplary embodiments of the present invention. The computer 705 is connected to a display 745 that may be a liquid crystal display (LCD) type computer screen, for example.

In an exemplary embodiment, the present invention may be implemented in software as an application program tangibly embodied on a program storage device (e.g., magnetic floppy disk, random access memory (RAM), compact disk read only memory (CD ROM), digital video disk (DVD), ROM, and flash memory). The application program may be uploaded to, and executed by, a machine comprising any suitable architecture.

It is to be understood that because some of the constituent system components and method steps depicted in the accompanying figures may be implemented in software, the actual connections between the system components (or the process steps) may differ depending on the manner in which the present invention is programmed. Given the teachings of the present invention provided herein, one of ordinary skill in the art will be able to contemplate these and similar implementations or configurations of the present invention.

While the present invention has been described in detail with reference to exemplary embodiments thereof, those skilled in the art will appreciate that various modifications and substitutions can be made thereto without departing from the spirit and scope of the present invention as set forth in the appended claims.

What is claimed is:

1. A method, comprising:
a first step of receiving a first image of a prostate in a planning phase, wherein the first image is acquired with a first imaging modality and is semi-automatically segmented, and wherein a binary mask and contours of the prostate are saved;
a second step of acquiring a second image of the prostate, wherein the second image is acquired with a second imaging modality;
a third step of performing an alignment to compensate for orientation misalignments between the first image and the second image, wherein the alignment uses user specified point correspondences on the prostate in the first and second images to compute rough translations and when three or more point correspondences are specified, a rigid registration estimate and an initial guess for the amount of anatomic deformations is computed automatically;
a fourth step of performing a manual adjustment of the alignment to account for translational misalignments between the first and second images by dragging slices from the first image to match content of the second image;
a fifth step of acquiring third images of the prostate, wherein the third images are acquired with the second imaging modality and are compounded into a three-dimensional (3D) image;
a sixth step of using an initial registration between the first and second images resulting from the alignment and the binary mask from the planning phase to segment the prostate in the compounded 3D image;
a seventh step of performing a second registration and then a third registration different from the second registration on distance maps generated from boundaries of the segmentations of the prostate in the first and second images;
an eighth step of transforming the first image along with its included annotations and segmentation structures onto the third images to produce a fourth image;
a ninth step of displaying the fourth image with a region of interest mapped thereon; and
monitoring quality of alignment of the region of interest in the displayed fourth image, and re-running the second step and the fifth through eighth steps if the quality deteriorates due to patient immobilization or anatomic shifts, or re-running the second through eighth steps if the quality deteriorates for large misalignments.

2. The method of claim 1, wherein the first imaging modality is magnetic resonance and the second imaging modality is ultrasound (US).

3. The method of claim 1, wherein the orientation of the first and second images comprise axial, sagittal or coronal.

4. The method of claim 1, wherein the alignment matches a center of the prostate in the first and second images.

5. The method of claim 1, wherein the third images of the prostate are acquired by a US fan sweep.

6. The method of claim 1, wherein the second registration is a rigid registration and the third registration is a deformable registration.

7. The method of claim 1, further comprising visually tracking a biopsy needle in the fourth image.

8. The method of claim 7, further comprising storing the location of the region of interest in memory and noting whether the region of interest has been biopsied.

9. The method of claim 1, further comprising displaying a projected needle path on the fourth image with the region of interest mapped thereon.

10. The method of claim 1, wherein the first image includes a plurality of regions of interest, the method further comprises storing locations of the regions of interest.

11. The method of claim 1, further comprising registering the fourth image to the compounded 3D image and then mapping a region of interest to the fourth image.

12. A system, comprising:
a memory device for storing a program; and
a processor in communication with the memory device, the processor operative with the program to:
perform a first step of receiving a first image of a prostate in a planning phase, wherein the first image is acquired with a first imaging modality and is semi-automatically segmented, and wherein a binary mask and contours of the prostate are saved;
perform a second step of receiving a second image of the prostate, wherein the second image is acquired with a second imaging modality;
perform a third step of receiving parameters of an alignment to compensate for orientation misalignments between the first image and the second image, wherein the alignment uses user specified point correspondences on the prostate in the first and second images to compute rough translations and when three or more point correspondences are specified, a rigid registration estimate and an initial guess for the amount of anatomic deformations is computed automatically;
perform a fourth step of receiving parameters corresponding to a manual adjustment of the alignment to account for translational misalignments between the first and second images, wherein the parameters are obtained by dragging slices from the first image to match content of the second image;
perform a fifth step of receiving third images of the prostate, wherein the third images are acquired with the second imaging modality and are compounded into a three-dimensional (3D) image;
perform a sixth step of using an initial registration between the first and second images resulting from the alignment and the binary mask from the planning stage to segment the prostate in the compounded 3D image;
perform a sixth step of performing a second registration and then a third registration different from the second registration on distance maps generated from boundaries of the segmentations of the prostate in the first and second images;
perform an eighth step of transforming the first image along with its included annotations and segmentation structures onto the third images to produce a fourth image;
performing a ninth step of displaying the fourth image with a region of interest mapped thereon; and
monitoring quality of alignment of the region of interest in the displayed fourth image, and re-running the second step and the fifth through eighth steps if the quality deteriorates due to patient immobilization or anatomic shifts, or re-running the second through eighth steps if the quality deteriorates for large misalignments.

13. The system of claim 12, further comprising an ultrasound device that provides the second image, third images or fourth image.

14. The system of claim 12, wherein the processor is further operative with the program to:
display an image of a biopsy needle in the fourth image.

15. The system of claim 12, further comprising a device that tracks a biopsy needle.

16. The system of claim 12, further comprising a device that tracks an ultrasound probe.

* * * * *